US00PP24041P3

(12) United States Plant Patent
Zaiger et al.

(10) Patent No.: US PP24,041 P3
(45) Date of Patent: Nov. 26, 2013

(54) INTERSPECIFIC TREE NAMED 'AUTUMN FANTASY'

(50) Latin Name: ***Interspecific Prunus* species**
Varietal Denomination: Autumn Fantasy

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 64 days.

(21) Appl. No.: 13/506,344

(22) Filed: Apr. 13, 2012

(65) Prior Publication Data

US 2013/0276178 P1 Oct. 17, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Productive and regular bearer of medium to large size fruit.
3. Fruit with very good flavor and eating quality.
4. Fruit with good handling and shipping quality.
5. Fruit with an average Brix of 22.0° and a good balance between acid and sugar.
6. Fruit maturing in the late maturity season.

1 Drawing Sheet

Botanical designation: Interspecific *Prunus* species.
Variety denomination: 'Autumn Fantasy'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plums, apricots, interspecifics and proprietary seedling selections, which are known to us, and mentioned herein, 'Mariposa' Plum (U.S. Plant Pat. No. 111), 'Amazon' Plum (U.S. Plant Pat. No. 2,043), 'Gold Brink' Apricot (U.S. Plant Pat. No. 8,433), 'Spring Giant' Apricot (U.S. Plant Pat. No. 5,138), 'Splash' Interspecific (U.S. Plant Pat. No. 14,583), 'Flavorfall' Interspecific (U.S. Plant Pat. No. 11,990), our proprietary seedling selections '4G1180' plumcot (non-patented), '42GA580' plumcot (non-patented), '329LN1' interspecific (non-patented), '24EB276' plum (non-patented) and '29Z574' interspecific (non-patented).

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species; [(*Prunus salicina*×(*Prunus salicina*×*Prunus armeniaca*))×*Prunus armeniaca*×(*Prunus salicina*×*Prunus armeniaca*))]. The present variety was selected from a first generation cross between our non-patented proprietary interspecifics '329LN1' and '29Z574'. The seed parent '329LN1' (non-patented) was developed by us from crossing the following; 'Amazon' Plum (U.S. Plant Pat. No. 2,043), 'Splash' Interspecific (U.S. Plant Pat. No. 14,583) and our proprietary plum seedling '24EB276' (non-patented). The pollen parent '29Z574' (non-patented) was developed by us from crossing the following; 'Gold Brink' Apricot (U.S. Plant Pat. No. 8,433), 'Spring Giant' Apricot (U.S. Plant Pat. No. 5,138), 'Mariposa' Plum (U.S. Plant Pat. No. 111) and the non-patented proprietary plumcots '4G1180' and '42GA580'. We planted and maintained a large number of these first generation seedlings, growing on their own root system. Under close and careful observation one such seedling, which is the present variety, exhibited distinct and desirable fruit and tree characteristics and was selected in 2007 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree which includes [(Plum×Plumcot)×(Apricot×Plumcot)] in its parentage is of large size, vigorous, upright growth and a productive and regular bearer of large size, yellow flesh, firm fruit with very good flavor and eating quality. The fruit is further characterized by having good storage and shipping quality and by maturing in the late season. In comparison to the seed parent '329LN1' (non-patented) the fruit of the new interspecific is larger in size, has firmer flesh and is approximately 13 days later in maturity. In comparison to the pollen parent '29Z574' (non-patented), the fruit of the new variety has dark red skin compared to orange skin, has glabrous compared to pubescent skin and is approximately 14 weeks later in maturity. In comparison to the commercial variety 'Flavorfall' Interspecific (U.S. Plant Pat. No. 11,990) the fruit of the new variety has a more desirable eating quality and is approximately 5 days later in maturity.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

- *Size*.—Large, usually pruned to 3 to 3.5 meters in height and width for economical harvesting of fruit. Varies with different cultural practices.
- *Vigor*.—Vigorous, tree growth of approximately 1.5 to 2 meters the first growing season. Varies with cultural practices, soil type, fertility and climatic conditions.
- *Form*.—Upright growth, usually prune to vase shape.
- *Branching habit*.—Upright, crotch angle approximately 30°, increases with heavy crop load.
- *Productivity*.—Productive, thinning and spacing of fruit desirable for market size fruit. Fruit set varies with climatic conditions during bloom time.
- *Bearer*.—Regular, adequate fruit set 3 consecutive years. No alternate bearing observed.
- *Fertility*.—Self-sterile, pollinator required.
- *Density*.—Medium dense, usually pruned to vase shape to increase sunlight and air movement to center of tree to enhance fruit color and health of fruit spurs.
- *Hardiness*.—Hardy in all stone fruit growing areas of California. Tree grown in USDA Hardiness Zone 9. Winter chilling requirement approximately 850 hours at or below 45° F.

Trunk:

- *Size*.—Large. Average circumference of 50.8 cm at 25 cm above ground on a 5 year old tree.
- *Stocky*.—Medium stocky.
- *Texture*.—Medium shaggy, becomes rougher with age.
- *Color*.—Varies from 2.5Y 6/2 to 5Y 5/2.

Branches:

- *Size*.—Medium. Average circumference 10.6 cm measured at 1.2 meters above ground. Crotch angle approximately 30°, increases with heavy crop.
- *Surface texture*.—New growth relatively smooth. Mature growth medium rough, roughness increases with age.
- *Lenticels*.—Average number 41 in a 25.8 sq cm area. Average length 1.8 mm. Average width 0.8 mm. Color varies from 7.5YR 5/8 to 7.5YR 5/10.
- *Color*.—New growth varies from 5GY 5/6 to 5GY 5/8. Old growth varies from 7.5YR 3/2 to 7.5YR 2/2, varies with age of growth.

Leaves:

- *Size*.—Medium. Average length 89.3 mm. Average width 39.3 mm.
- *Form*.—Oblanceolate.
- *Apex*.—Acuminate.
- *Base*.—Cuneate.
- *Margin*.—Serrate.
- *Thickness*.—Medium.
- *Surface texture*.—Upper surface relatively smooth, slight indentations over midrib and leaf veins. Lower surface relatively smooth, except for small ridges created by midrib and pinnate venation. Both upper and lower surfaces glabrous.
- *Petiole*.—Average length 18.5 mm. Average width 1.4 mm. Longitudinally grooved. Surface glabrous. Color varies from 5GY 6/4 to 5GY 6/6.
- *Glands*.—Globose. Size — small. Average length 0.1 mm. Average width 0.1 mm. Average number 2, varies from 1 to 3. Located primarily on the upper portion of the petiole and the base of leaf blade. Color varies from 5GY 5/4 to 7.5GY 5/4.
- *Stipules*.—Average number 2. Average length 2.9 mm. Edges pectinate. Color varies from 5GY 7/6 to 5GY 6/6.
- *Color*.—Upper surface varies from 2.5GY 2/2 to 5GY 2/2. Lower surface varies from 2.5GY 4/2 to 5GY 4/2. Midvein color varies from 2.5GY 7/2 to 2.5GY 7/4.

Flower buds:

- *Size*.—Medium, Average length 9.1 mm. Average diameter 5.6 mm.
- *Hardiness*.—Hardy with respect to California winters.
- *Form*.—Conical, becoming elongated as it matures.
- *Pedicel*.—Average length 11.5 mm. Average width 0.7 mm. Color varies from 2.5GY 5/8 to 5GY 5/8.
- *Color*.—N 9.5/ (white).
- *Number of buds per spur*.—Average 10, varies from 7 to 14. Varies with age of spur.

Flowers:

- *Blooming period*.—Date of First Bloom Mar. 10, 2011. Date of Petal Fall Mar. 21, 2011, varies slightly with climatic conditions.

*Size*.—Medium. Average height 11.2 mm. Average diameter 19.0 mm.

*Petals*.—Normally 5, alternately arranged to the sepals. Size — medium. Average length 10.2 mm. Average width 6.5 mm. Form varies from globose to slightly elongated. Both upper and lower surfaces glabrous. Color N 9.5/ (white).

*Sepals*.—Normally 5, alternately arranged to petals. Size — small to medium. Average length 3.4 mm. Average width 2.5 mm. Shape — triangular, apex rounded. Margin entire. Both upper and lower surfaces glabrous. Color — upper surface varies from 2.5GY 6/8 to 5GY 6/8. Lower surface varies from 5GY 6/8 to 5GY 5/8.

*Stamens*.—Average number per flower 29, varies from 28 to 32. Average filament length 8.3 mm. Filament color N 9.5/ (white). Anther color varies from 5YR 6/10 to 5YR 5/10.

*Pollen*.—Present, self-sterile, pollinator required. Color varies from 2.5Y 7/10 to 2.5Y 7/12.

*Pistil*.—Normally one. Surface glabrous. Average length 9.4 mm. Position of stigma approximately 1.0 mm below anthers. Color varies from 10Y 7/8 to 2.5GY 7/8.

*Fragrance*.—Heavy aroma.

*Color*.—N 9.5/ (white).

*Number flowers per flower bud*.—Average number 3, varies from 1 to 4.

*Pedicel*.—Average length 13.3 mm. Average width 0.8 mm. Surface glabrous. Color varies from 2.5GY 6/6 to 2.5GY 6/8.

Fruit:

*Maturity when described*.—Firm ripe.

*Date of first picking*.—Oct. 10, 2011.

*Date of last picking*.—Oct. 20, 2011, varies slightly with climatic conditions.

*Size*.—Medium to large. Average diameter axially 60.9 mm. Average transversely in suture plane 55.7 mm. Average weight 119.8 grams, varies slightly with fertility of the soil, amount of thinning and climatic conditions.

*Form*.—Globose to slightly elongated.

*Suture*.—Slightly lipped, extends from base to apex.

*Ventral surface*.—Slightly lipped.

*Apex*.—Rounded to slightly retuse.

*Base*.—Flat to very slightly retuse.

*Stem cavity*.—Rounded to slightly elongated in suture plane. Average depth 4.4 mm. Average diameter 5.6 mm.

Stem:

*Size*.—Medium. Average length 16.1 mm. Average diameter 1.6 mm.

*Color*.—Varies from 2.5GY 5/8 to 5GY 5/6.

Flesh:

*Ripens*.—Evenly.

*Texture*.—Firm, meaty.

*Fibers*.—Few, small, tender.

*Firmness*.—Good, comparable to commercial varieties.

*Aroma*.—Moderate.

*Amydgalin*.—Undetected.

*Eating quality*.—Very good.

*Flavor*.—Very good, good balance between sugar and acid.

*Juice*.—Moderate to heavy amount, enhances flavor.

*Brix*.—Average Brix 22.5°, varies slightly with amount of fruit per tree and climatic conditions.

*Color*.—Yellow, varies from 10YR 7/6 to 2.5Y 8/6.

*Pit cavity*.—Average length 27.5 mm. Average width 18.5 mm. Average depth 6.0 mm. Color varies from 10R 5/8 to 10R 4/8.

Skin:

*Thickness*.—Medium.

*Surface*.—Smooth.

*Bloom*.—Moderate amount.

*Tendency to crack*.—None to very slight with heavy rain, varies with fruit maturity.

*Color*.—Ground color yellow, varies from 10YR 8/6 to 2.5Y 8.5/6. Overspread with 5R 2/2 to 7.5R 2/4.

*Tenacity*.—Tenacious to flesh.

*Astringency*.—Undetected.

Stone:

*Type*.—Clingstone.

*Size*.—Medium. Average length 26.5 mm. Average width 17.1 mm. Average thickness 10.4 mm.

*Form*.—Ovoid.

*Base*.—Flat.

*Apex*.—Pointed. Average length 2.1 mm.

*Surface*.—Slightly pitted throughout.

*Sides*.—Unequal, one side extending further from the suture plane.

*Ridges*.—A very small ridge on each side of suture extending from base to apex.

*Tendency to split*.—None.

*Color*.—Varies from 7.5R 3/8 to 5YR 3/6, when dry.

Kernel:

*Size*.—Small to medium. Average length 14.5 mm. Average width 9.0 mm. Average depth 5.5 mm.

*Form*.—Ovoid.

*Viability*.—Viable, complete embryo development.

*Skin*.—Color varies from 7.5YR 5/6 to 10YR 6/6.

*Taste*.—Bitter.

Use:

*Dessert*.—Market — Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

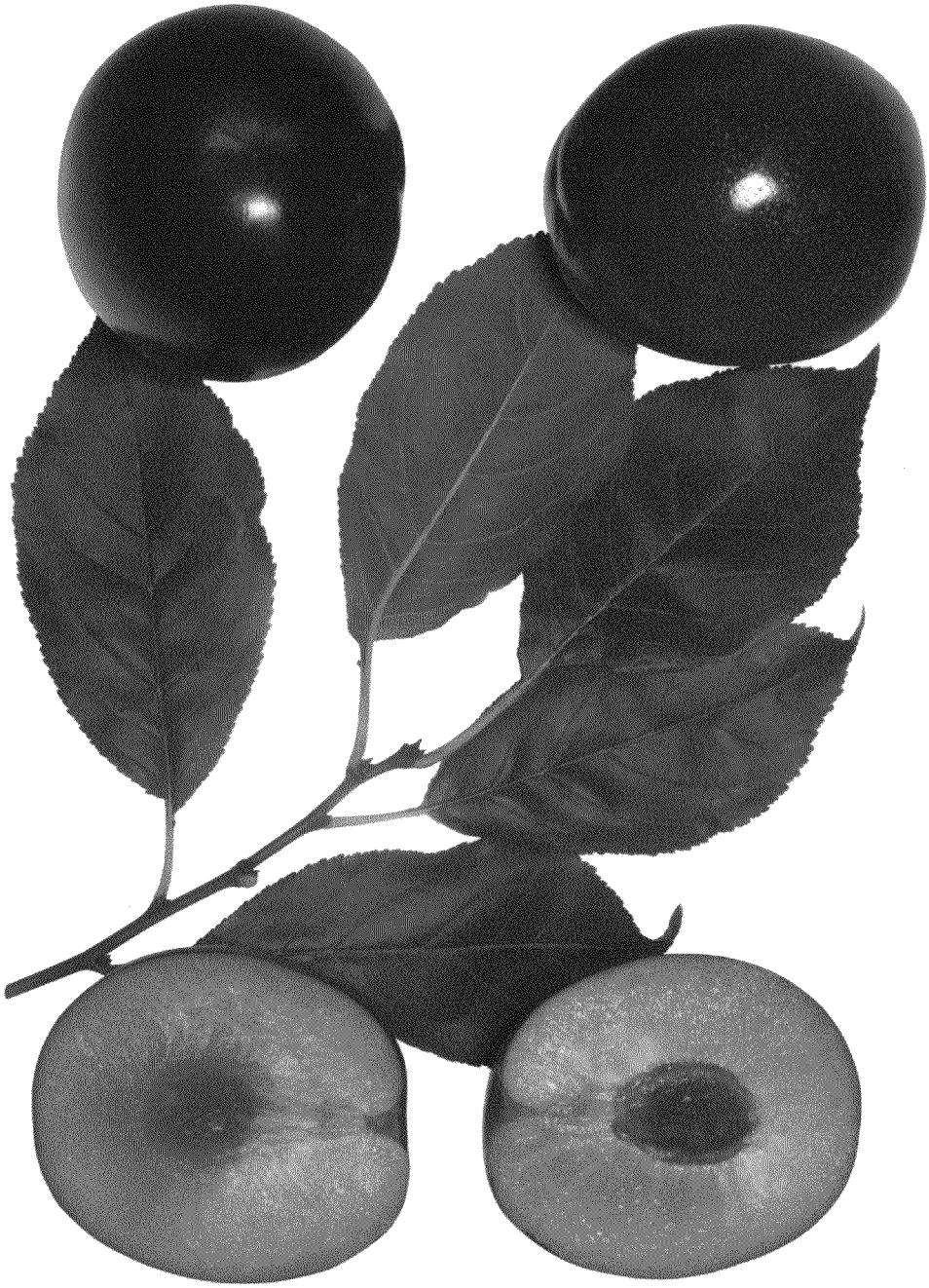

* * * * *